US005593417A

United States Patent [19]
Rhodes

[11] Patent Number: 5,593,417
[45] Date of Patent: Jan. 14, 1997

[54] INTRAVASCULAR STENT WITH SECURE MOUNTING MEANS

[76] Inventor: Valentine J. Rhodes, 608 Winding River Rd., Bricktown, N.J. 08723

[21] Appl. No.: 562,727

[22] Filed: Nov. 27, 1995

[51] Int. Cl.⁶ ................................................. A61M 29/00
[52] U.S. Cl. .............................. 606/191; 606/198; 623/1; 623/12
[58] Field of Search .................. 606/198, 191, 606/194, 195, 108; 623/1, 12; 604/96, 104

[56]  References Cited

U.S. PATENT DOCUMENTS

| | | |
|---|---|---|
| 3,657,744 | 4/1972 | Ersek . |
| 4,047,252 | 9/1977 | Liebig et al. . |
| 4,503,569 | 3/1985 | Dotter . |
| 4,512,338 | 4/1985 | Balko et al. . |
| 4,580,568 | 4/1986 | Gianturco . |
| 4,655,771 | 4/1987 | Wallsten . |
| 4,733,665 | 3/1988 | Palmaz . |
| 4,740,207 | 4/1988 | Kreamer . |
| 4,776,337 | 10/1988 | Palmaz . |
| 4,795,458 | 1/1989 | Regan . |
| 4,830,003 | 5/1989 | Wolff et al. . |
| 4,856,516 | 8/1989 | Hillstead . |
| 4,994,071 | 2/1991 | MacGregor . |
| 5,035,706 | 7/1991 | Giantureo et al. . |
| 5,122,154 | 6/1992 | Rhodes ........................................ 623/1 |
| 5,167,614 | 12/1992 | Tessmann et al. . |
| 5,207,695 | 5/1993 | Trout, III . |
| 5,275,622 | 1/1994 | Lazarus et al. . |
| 5,306,286 | 4/1994 | Stack et al. . |
| 5,383,892 | 1/1995 | Cardon et al. . |
| 5,387,235 | 2/1995 | Chuter . |
| 5,397,345 | 3/1995 | Lazarus . |
| 5,423,885 | 6/1995 | Williams . |

*Primary Examiner*—Michael Powell Buiz
*Assistant Examiner*—Kevin Truong
*Attorney, Agent, or Firm*—Caesar, Rivise, Bernstein, Cohen & Pokotilow, Ltd.

[57]  ABSTRACT

An endovascular graft for securement within a vessel, duct, or lumen of a living being. The graft comprises a tubular graft sleeve and a plurality of ring-like stents mounted on the outer surface of the sleeve. Anchoring projections are provided on the outer surface of the stents. The graft sleeve has a passageway extending therethrough, which when the graft is located within the vessel, duct, or lumen serves to carry body fluid, e.g., blood, through it in a single direction. This action produces a force on the tubular sleeve and the plural stents mounted thereon. The anchoring projections extend outward from the outer surface of the stents and are arranged for engagement with the interior of the wall of the vessel, duct, or lumen. The anchoring projections are preferentially oriented to include portions extending at an acute angle to the direction of the fluid flow to tightly engage the interior of the wall of the vessel, duct, or lumen under the force applied by the fluid flowing through the device.

15 Claims, 3 Drawing Sheets

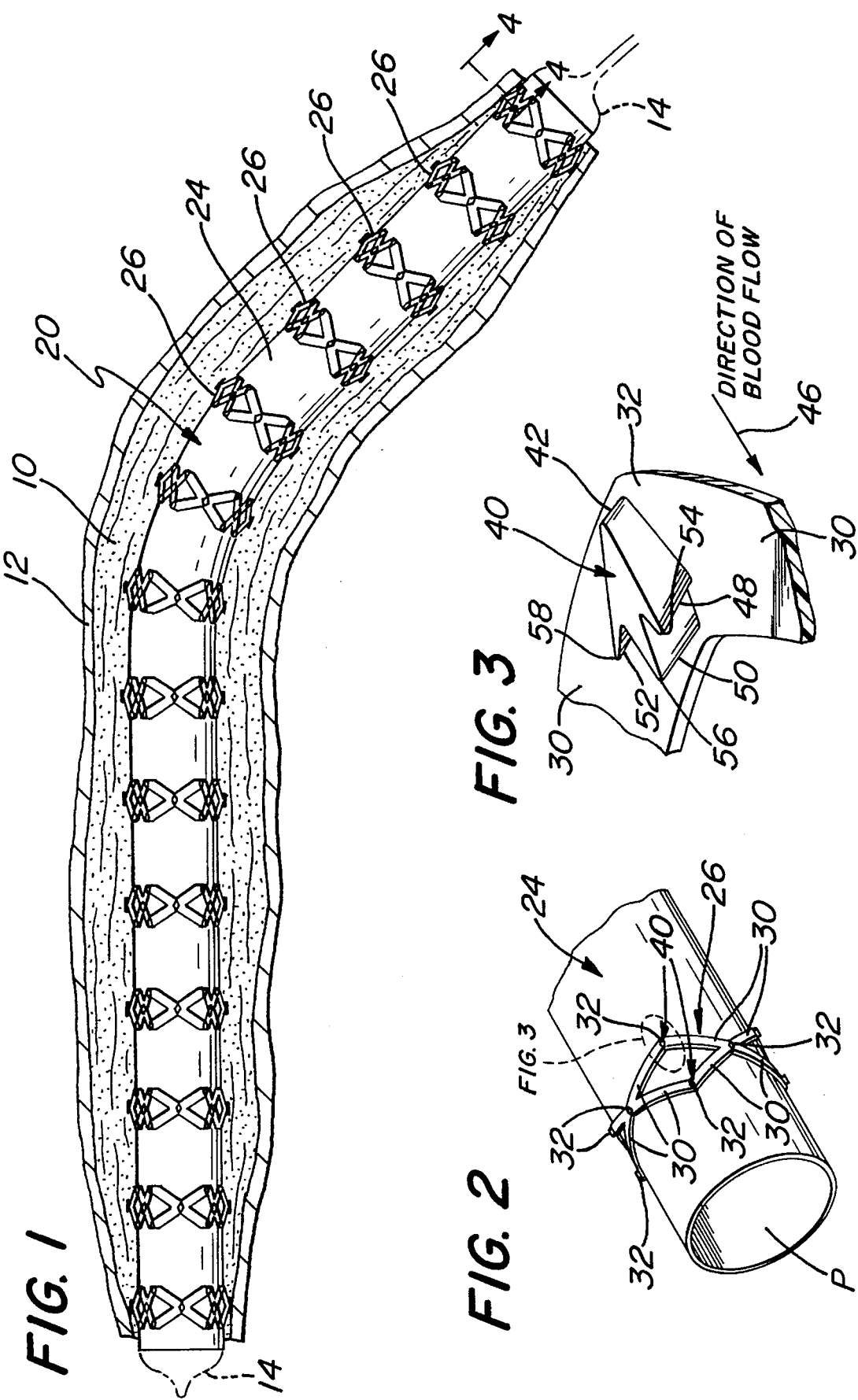

INTRAVASCULAR STENT WITH SECURE MOUNTING MEANS

BACKGROUND OF THE INVENTION

The invention relates generally to medical devices and methods of use in vessels, ducts or lumens of living beings, and more particularly to expandable grafts and methods of use for opening restrictions therein, e.g., revascularizing stenotic arteries.

Percutaneous balloon intraluminal dilation of vascular stenoses or blockages through the use of angioplasty balloon catheters have proven quite successful. However, such procedures are not without risk or some drawbacks. In particular, the angioplasty balloon is inflated within the narrowed vessel in order to shear and disrupt the wall components of the vessel to obtain a large lumen. The relative incompressible plaque remains unaltered by this procedure, while the more elastic medial and adventitial layers of the body passageways stretch around the plaque. This process produces subintimal dissection, splitting, tearing, and disruption of the intact intima and wall layers. If the section forms a transverse tear it produces a flap which may lift away from the artery and may produce an obstruction to the lumen, and therefore make the blockage and stenosis worse. In addition, if there is a heavy plaque on one side of the artery wall (as occurs in 80% of atherosclerotic stenotic lesions) the thinner layer may be disrupted by the inflation of the balloon and cause hemorrhage. Moreover, after the balloon is decompressed any loose material may dislodge completely and act as an embolic source to occlude the lumen of the vessel distally to such an acute extent as to result in significant emergency ischemic conditions. This situation has occurred frequently enough to pose a significant risk to the patient.

Laser assisted balloon angioplasty has been used frequently in recent years to revascularize a totally occluded vessel. In particular the occlusion is opened with the laser and then the opening is expanded further by balloon angioplasty. One of the problems with this revascularization procedure is that the laser causes intimal damage along with the balloon. Moreover, this procedure has only been useful for short segment occlusions. When long segment occlusions are attacked by this procedure the reocclusion rate has proven to be very high, and sometimes even made worse.

In both simple balloon angioplasty and in laser assisted balloon angioplasty there is a high incidence of recurrence of the stenosis or obstruction. This is, of course, in addition to the risk of embolization and acute occlusion and disruption of the artery with massive hemorrhage. In addition, there are certain vessels bearing areas of plaque which are not amenable to balloon angioplasty because of the fact that they are orificial plaques, i.e., plaques at the orifice of a branch artery. Thus, when the balloon is inserted across this type of lesion and inflated, it inflates differentially, that is the portion of the balloon in the larger part of the artery inflates more than the portion of the balloon crossing the narrowed or stenotic segment. In fact the portion of the balloon crossing the narrowed or stenotic segment frequently does not inflate at all. Therefore, unsuccessful attempts at inflation are the rule rather than the exception. This is particularly true in attempting the revascularization of renal arteries or the superior mesenteric artery.

Intraluminal endovascular grafting has been demonstrated by experimentation to present an alternative to conventional vascular bypass surgery. Such "grafting" involves either the percutaneous insertion into a blood vessel of a tubular prosthetic graft or stent or an open insertion thereof through a short segment exposed portion of the blood vessel. The graft is typically positioned in a predetermined location within the blood vessel and then expanded by a catheter delivery system. However, the use of conventional bypass grafts exhibits the tendency of recurring stenosis. Such restenosis may progress to the point where the graft fails. In this connection the cause of stenosis in bypass grafts (including dialysis access fistulas) is usually fibro-intimal hyperplasia (also known as pseudo-intimal hyperplasia or neo-intimal hyperplasia), a very elastic fibrous tissue which recoLlapses almost immediately upon relaxation of the balloon. Such tissues are, however, ideal for being supported by a stent (i.e., a self supporting member).

Accordingly, it has been suggested, and there is some activity now occurring, to use stents in revascularization procedures to preclude restenosis. Another useful area of stent application is percutaneous angioplasty of Takayasu arteritis and neurofibromatosis arterial stenoses, since those conditions may show poor response and reoccurrence which is very high due to the fibrotic nature of these lesions.

Examples of various types of expandable grafts/stents are disclosed in U.S. Pat. Nos. 3,657,744 (Fursek); 4,047,252 (Liebig et al.); 4,503,569 (Dotter); 4,512,338 (Balko et al.); 4,580,568 (Gianturo); 4,655,771 (Wallsten); 4,733,665 (Palmaz); 4,740,207 (Kreamer); 4,766,337 (Palmaz); 4,795,458 (Regan); 4,830,003 (Wolff et al.); 4,856,516 (Hillstead); 4,994,071 (MacGregor); and 5,035,706 (Giantureo et al.), and in the following literature: "Balloon-Expandable Intracoronary Stents in the Adult Dog", Circulation, August 1987, pages 450–456, Vol 76, No 2; "Normal and Stenotic Renal Arteries: Experimental Balloon-expandable Intraluminal Stenting", Radiology, 1987, pages 705–708, Vol 164, No 3; "A Titanium-Nickel Alloy Intravascular Endoprothesis", Transactions American Society of Artificial Internal Organs, 1988, pages 399–403, Vol. XXXIV; "Self-Expanding Endovascular Stent in Experimental Atherosclerosis", Radiology, March 1989, pages 773–778, Vol. 170, No. 3; "Emergency Stenting for Acute Occlusion After Coronary Balloon Angioplasty", Circulation, Nov. 1988, pages 1121–1127, Vol 78, No 5; "Intravascular Stents for Angioplasty", CARDIO, December 1987; "Intra-Arterial Stenting in the Atherosclerotic Rabbit", Circulation, September 1988, pages 646–653, Vol 78, No 3; "Intravascular Stents to Prevent Occlusion and Restenosis After Transluminal Angioplasty", The New England Journal of Medicine, March 1987, pages 701–706, Vol. 316, No. 12; "A Polyester Intravascular Stent for Maintaining Luminal Patency", Texas Heart Institute Journal, Nov. 1, 1988, pages 12–16, Vol. 15. "Post Dilatation Stenting; Early Experience of the Use of an Endocoronary Prosthesis to Prevent Restenosis Reoccurrence After Angioplasty", J. Cardiovasc. Surg. 28, 1987, Session 8: CARDIAC—CORONARY (II); "Intravascular Stents to Prevent Occlusion and Restenosis After Transluminal Angioplasty", Abstract from New England Journal of Medicine 1987, Volume 316, pages 701–706; "Vascular Stenting in Normal and Atherosclerotic Rabbits", Circulation, February 1990, Vol 81, No. 2, pages 667–683; Treatment of Major Venous Obstruction with an Expandable Endoluminal Spiral Prosthesis, J. Cardiovasc. Surg. 30, 1989, pages 112–117; and Venous Stenases in Dialysis Shunts: Treatment with Self-Expanding Metallic Stents, Radiology, February 1989, Vol. 170, No. 2, pages 401–405.

In my U.S. Pat. No. 5,122,154, whose disclosure is incorporated by reference herein, there is disclosed an intraluminal bypass graft which overcomes many of the disadvantages of the prior art devices. That bypass graft is arranged for placement in a blood vessel, duct, or lumen, to hold it open. The graft comprises a sleeve having plural stents thereon. The sleeve is an elongated tubular member formed of a conventional graft material which is flexible and impervious to the ingrowth of tissue therein. Each stent is a generally ring-like member formed a plurality of interconnected movable links and is mounted about the periphery of a surface, e.g., inner or outer, of the sleeve at selected points along the sleeve to form respective spaced first sleeve sections. Each of the first sections extends for only a portion of the length of the graft, thereby leaving a plurality of second sleeve sections interposed between the first sleeve sections. The stents and the sleeve are arranged to be expanded, e.g., by a balloon catheter, from a compact state to an expanded state to increase the inner cross sectional area diameter of the sleeve. In the expanded state the stents are resistant to contraction back to the compact state. The graft is able to bend with respect to its longitudinal axis to enable it to be readily accommodated within a curved blood vessel, duct, or lumen.

The graft of my aforementioned patent makes use of some anchoring means, e.g., small dome shaped projections, for aiding in the securement of the graft in place within the vessel, duct, or lumen. While such anchoring means are believed effective for their intended purpose, they never the less appear to be amenable to improvement insofar as graft retention is concerned.

Various U.S. Pat. Nos. have disclosed devices for intraluminar location and securement, which devices include plural projections for effecting such securement, such as: 5,167,614 (Tessman et al.); 5,207,695 (Trout III); 5,275,622 (Lazarus et al ); 5,306,286 (Stack et al ); 5,383,892 (Cardon et al.); 5,387,235 (Chuter); 5,397,345 (Lazarus); and 5,423,885 (Williams).

Notwithstanding the foregoing, a need exists for means for ensuring good retention from migration for intraluminal grafts.

OBJECTS OF THE INVENTION

It is a general object of this invention to provide intraluminal medical devices and methods of use of the same which overcome the disadvantages of the prior art.

It is a further object of this invention to provide anchoring means for intraluminal medical devices, e.g., endovascular grafts, stents, etc, arranged to be fixedly secured within a vessel, duct, or lumen of a living being.

It is a further object of this invention to provide anchoring means for intraluminal medical devices to be secured within in a vessel, duct, or lumen of a living being, and which anchoring means is simple in construction.

It is a further object of this invention to provide anchoring means for intraluminal medical devices to be secured within in a vessel, duct, or lumen of a living being, and which anchoring means does not pose a significant risk of perforating the tissue of the vessel, duct, or lumen.

SUMMARY OF THE INVENTION

These and other objects of this invention are achieved by providing an intraluminal medical device for securement within a vessel, duct, or lumen of a living being. The vessel, duct, or lumen has an interior surface and is arranged to have a body fluid, e.g., blood, flow therethrough in a first direction.

The medical device basically comprising a tubular member and anchoring means. The tubular member has a passageway extending therethrough and outer periphery, and is arranged to have fluid flow through its passageway in a first direction when the device is located within the vessel, duct, or lumen, whereupon a force is applied to the tubular member. The anchoring means are located adjacent the outer periphery of the tubular member and comprise plural projections.

The projections are arranged for engagement with the interior of the wall of the vessel, duct, or lumen, and are preferentially oriented to include portions extending at an acute angle to the first direction. These portions tightly engage the interior of the wall of the vessel, duct, or lumen under the force applied to the tubular member by the fluid flowing through the passageway in the first direction. In particular, the force applied to the tubular member by the fluid flowing through the passageway produces on each of the preferentially oriented projections a force component extending in the first direction (the direction of fluid, e.g., blood, flow), and a force component extending perpendicularly (i.e., radially) to the first direction, to thereby cause the projections to tightly engage, e.g., burrow slightly into, the interior of the wall of the vessel, duct, or lumen to thereby fixedly secure the device in place.

In accordance with the preferred embodiment of the invention the device is, endovascular graft, wherein the tubular member comprises a graft sleeve having plurality of ring-like stents disposed about the outer periphery thereof. The anchoring means are located on the outer surface of the stents. The stents and the graft sleeve are expandable from a compact state to an expanded state, whereupon the anchoring means engage the interior of the vessel, duct, or lumen. The flow of fluid, e.g., blood, through the device applies the force through the graft sleeve and the stents to the anchoring projections, to cause the anchoring projections to tightly engage, e.g., burrow slightly into, the interior of the vessel, duct, or lumen.

DESCRIPTION OF THE DRAWINGS

Other objects and many attendant advantages of this invention will become readily appreciated as the same becomes better understood by reference to the following detailed description when considered in connection with the accompanying drawings wherein:

FIG. 1 is a longitudinal view, partially in section, of an artery revascularized by an endovascular bypass graft constructed in accordance with the subject invention, with the graft being shown in its expanded state;

FIG. 2 is an enlarged isometric view of a portion of the endovascular bypass graft shown in FIG. 1;

FIG. 3 is a more greatly enlarged isometric view of a stent portion of the graft shown within the area bounded by the broken lines bearing the designation 3 in FIG. 2;

DETAILED DESCRIPTION OF THE PREFERRED EMBODIMENTS

Figure 4:
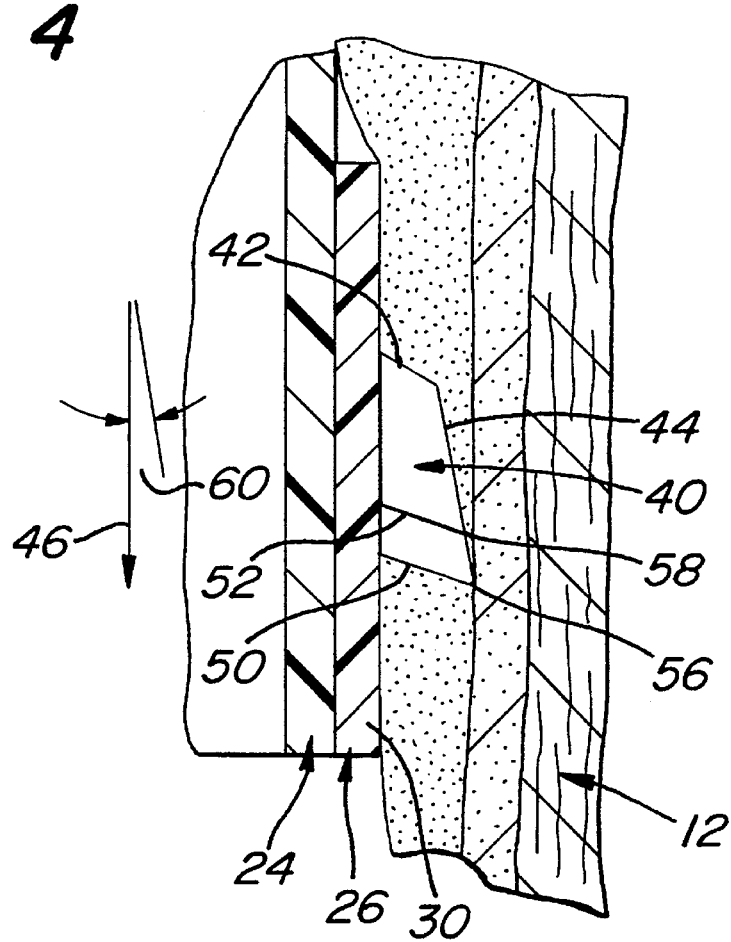
FIG. 4 is a greatly enlarged sectional view taken along line 4—4 of FIG. 1.

Referring now to various figures of the drawing where like reference numerals refer to like parts there is shown at 20 in FIG. 1 an expandable, intraluminal bypass graft device constructed in accordance with this invention. The graft device 20 is constructed in accordance with the teachings of my aforementioned patent, except for the means for fixedly holding it in place within the vessel, duct, or lumen. In this regard the subject invention makes use of anchoring means, to be described later, which offer an improvement in retention over the "protuberances" disclosed in my aforementioned patent.

Before describing the improved anchoring means of this invention a brief description of the graft device is in order. To that end, the graft device 20 is particularly suited for revascularizing lesions, e.g., atherosclerotic plaque lesions, in arteries. However, it should be appreciated that the graft device as disclosed herein can be used for other intraluminal applications, as well. Moreover, the anchoring means of this invention can be used in other intraluminal medical devices. In this regard, the anchoring means can be incorporated into any intraluminal device for securement in a vessel, duct, or lumen in the body of a living being, and through which a body fluid will flow.

In FIG. 1 the endovascular graft device 20 is shown in a typical long segment lesion 10 of an artery 12. The lesion is made up of atherosclerotic deposits forming a small or narrow, restricted passageway for flow of blood therethrough. The endovascular graft 20 is configured so that it is initially in a compact or compressed state shown in cross section in FIG. 5. In that state it is arranged to be readily inserted into the arterial passageway, via any conventional means, e.g., a balloon catheter 14 shown in phantom in FIG. 1 and positioned so that it extends through the restriction. Once in position the graft 20 is expanded to an expanded state, like that shown in FIG. 1 by inflating the balloon 14. In the maximum expanded state the graft 20 has a central passageway P (FIG. 2) which is of maximum internal cross-sectional area. When the graft 20 is in the expanded state a substantially greater cross-sectional area of the arterial section is open to the free flow of blood therethrough than prior to the use of the graft 20.

Figure 5:
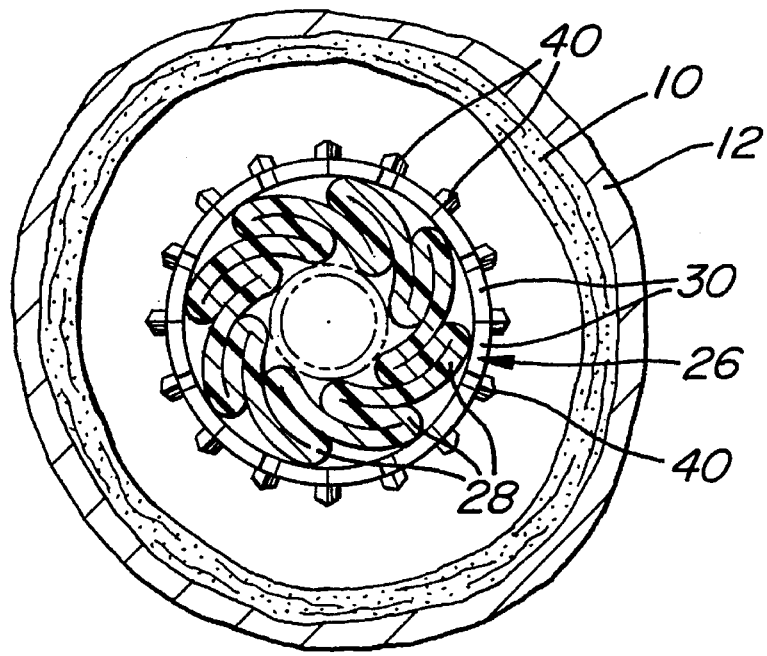
FIG. 5 is a cross-sectional view through the artery of FIG. 1 and showing the graft in its compact state, prior to expansion.

As discussed earlier, the expansion of the graft 20 from a compacted state shown in FIG. 5 to the expanded state shown in FIG. 1 is preferably accomplished by a conventional balloon catheter 14. However, any suitable other expansion means or instrument (not shown) may be used.

Referring now to FIGS. 1, 2 and 5, it can be seen that the graft device 20 basically comprises an elongated tubular member or sleeve 24 having a plurality of expandable, ring-like, stent members or sections 26 located at equidistantly spaced positions along the longitudinal length of the sleeve member 24. The sleeve member is formed of a thin and highly flexible material, such as expanded polytetrafloroethylene used for conventional vascular grafts. Examples of such prior art graft materials are those sold by W. C. Gore and Company under the trademark GORTEX or those sold by Impra, Inc. under the trademark IMPRAGRAFT.

The sleeve 24 is configured so that it is pleated, i.e., it includes a plurality of longitudinally extending pleats 28. Each of the pleats extends the entire length of the graft 20.

The pleated tube or sleeve is normally in a compacted state as shown in FIG. 5, that is each of the pleats overlies and abuts a contiguous portion of an immediately adjacent pleat. The sleeve is arranged to be expanded to a maximum expanded state wherein its pleats open up and form a generally continuous curved, e.g., cylindrical, inner and outer surface. The inner surface forms the passageway P through the graft device through which blood will flow.

When the graft is in the compacted state of FIG. 5 its outside diameter is substantially less than when it is in the expanded state. Moreover, when the graft sleeve is in its expanded state, its internal cross-sectional area is substantially greater than in the compact state. It must be pointed out at this juncture that the graft may be partially expanded in an artery to be revascularized, whereupon its pleats do not fully open up (flatten out). In such a case the internal cross sectional area is less than in the fully expanded state, but more than in the compacted state, and thus still permits the freer flow of blood therethrough than would flow through natural passageway in the restriction.

The spaced stent members 26 serve as the means for holding or retaining the sleeve 24 in any desired expanded state (i.e., from a slightly partially expanded state, not shown, to the fully expanded state like shown in FIG. 1). Thus, as can be seen best in FIG. 3, each stent member 26 basically comprises a plurality of interconnected links 30. Each of the links is an elongated rigid member formed of stainless steel or some other suitable biocompatible material, e.g., tantalum, plastic. Each link has a pair of ends and is joined to an associated link via a pivotable joint 32. Each joint 32 is made up of one end of one link and the other end of the immediately adjacent link. The link ends are connected by any suitable means, e.g., a deformable member, a pin, etc., to enable the links to pivot outward with respect to each other so that the angle therebetween increases, yet which precludes the links from pivoting backward toward each other. When so arranged the links form a zig-zag pattern. In the embodiment shown herein each joint 32 comprises the material making up the links themselves, and such material is deformable, but not resilient, so that once deformed, i.e., the links pivoted outward, it doesn't return to its previous configuration.

As should be appreciated by those skilled in the art when the links are pivoted outward with respect to each other the stent 26 expands from its compact state to the expanded state, like that shown in FIG. 1.

In accordance with a preferred aspect of this invention the joints 42 at the interfaces of each of the links of the stents are arranged to maintain any angular orientation between the connected links from the compact state to the maximum expanded state such that once the stents 26 are expanded to any expanded state (whether partial or full) movement back to the compact state is precluded.

The links of the stents of this invention serve to hold the sleeve member 24 in its expanded state. To that end, in the embodiment shown herein each of the stents is mounted on the outside of the sleeve, whereupon the links of those stents are connected to one or more pleats 28 externally of the sleeve, i.e., on the outer surface of the sleeve. If desired, the stents 26 could be disposed or mounted within the sleeve. In the later case the links can be connected internally of the sleeve. Moreover, if desired, the stents may be completely encased in the graft material forming the sleeve.

Figure 6:
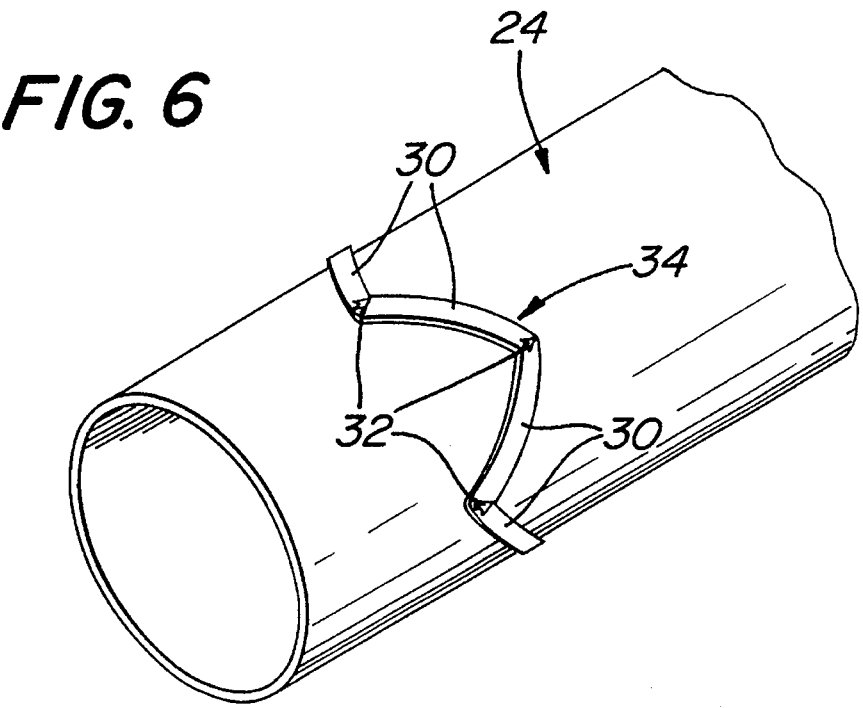
FIG. 6 is an enlarged isometric view similar to FIG. 2 of another alternative embodiment of endovascular bypass graft constructed in accordance with this invention.

In the preferred embodiment shown in FIG. 1, each of the stents 26 is made up of pairs of interconnected links to form two zig-zag patterns sharing common joints, thereby creating a diamond-like pattern stent. In FIG. 6 there is shown an alternative graft using plural spaced stents 34. Each stent 34 comprises a plurality of links 30 which are interconnected via joints 32 (like that of the embodiment shown in FIG. 1), except the links are not paired, so that a single zig-zag pattern is produced instead of the diamond-like pattern of FIG. 1. In all other regards the graft device utilizing stents 34 is the same as that described heretofore.

In order to help hold or secure the graft in position in the artery (or lumen or duct) once the graft has been expanded, the graft includes the heretofore mentioned anchoring means. Such anchoring means comprise plural protuberances or projections 40. In the preferred embodiments disclosed herein the protuberances are mounted on the stents 26 and 34. In particular, each stent includes a plurality of protuberances or projections projecting slightly outward therefrom and from the outer surface of the graft sleeve. As will be described in detail later, these projections 40 are preferentially oriented so that the force of the fluid, e.g., blood, flowing through the graft device 20 is applied to them to cause them to tightly engage the interior of the wall making up the vessel, duct, or lumen. In particular, as will be described in detail with respect to FIGS. 3 and 4, the projections 40 include portions extending at an acute angle to the direction which the fluid flows through the device when the device is positioned intraluminally, whereupon the force applied to the projections by that fluid flow includes a force component extending in the direction of the fluid flow and a force component extending radially, i.e., perpendicularly to the direction of the fluid flow. This action causes the projections to tightly engage, e.g., burrow slightly into, the interior of the vessel, duct, or lumen to fixedly secure the device in place.

Before describing the construction of the projections 40, it should be pointed out, that they can be located on any exterior portion of the device 20 in order to engage the interior of the vessel, duct, or lumen to secure the device in place. In the preferred embodiment shown herein the projections 40 are located on the stents, and in particular, at the joints of the stents. This is merely exemplary. Thus, the projections can be located at any suitable portion on the stents, so long as when the stent is expanded the projections 40 are properly preferentially oriented (as will be described later). Moreover, the mechanism, e.g., pivot pin, deformable member, etc., forming each joint of the stent may itself form a projection.

In the case of an interiorly located stent, i.e., a device wherein the stent is located on the interior of the sleeve or embedded within the material making up the sleeve (as discussed earlier), if the interior stent is to include the projections 40 as a part of it, those projections must extend through the sleeve so as to be located on the outer surface of the sleeve. Another suitable arrangement for an device using a interiorly located stent is to utilize projections which are not part of the stent itself. In such an alternative arrangement the projections may form a separate component of the device 20, e.g., be separate elements, mounted on the outer surface of the sleeve in order to engage the interior of the vessel, duct, or lumen.

Referring now to FIGS. 3 and 4, the details of the projections 40 will now be described. As can be seen therein each projection is of a generally "arrow head" shape when viewed in plan. In particular, each projection includes a leading edge 42 defining the "tip" of the "arrow-head." The leading edge 42 extends upward at an acute angle to the exterior surface of the stent and terminates at the top surface 44 of the projection. The top surface 44 is generally planar and inclines upward in the direction of blood flow. That direction is designated by the arrow 46 in FIGS. 3 and 4. The trailing edges of each projection 40 are designated by the reference numbers 48, 50, and 52 (FIG. 3), and each inclines upward in the direction of the blood flow to terminate at the top surface 44 in respective penetration points 54, 56, and 58, respectively. Thus, as can be appreciated each of the projections 40 includes portions which are preferentially oriented at an acute angle to the direction of blood flow. The acute angle is shown in FIG. 4 and designated by the reference numeral 60.

As will be appreciated by those skilled in the art, with blood (or some other fluid) flowing through the device 20 in the direction of arrow 46 a force will be applied by that flow to the interior surface of the sleeve 24, and from there through the stents to the projections 40. The force applied to the projections 40 will have a force component directed in the direction of the fluid flow, and a force component perpendicularly thereto, i.e., extending radially outward. Thus, the flow of fluid, e.g., blood, through the device 20 will tend to force the projections 40 into good engagement with the wall 12 of the vessel, duct, or lumen. In the embodiment shown herein the projections penetrate or burrow slightly into the artery wall, as shown clearly in FIG. 4. Such penetration may not be necessary for good resistance to migration of the device. If some penetration is deemed desirable the height of the projections is selected so that their penetrating points do not penetrate too deeply into the artery wall. In this regard, the height of the projections is selected so that they do not penetrate into the adventicial or medial layers of the artery wall, but can penetrate its intima. It is anticipated that for applications within the very largest arteries, such as the abdominal aorta, that the height of the projections will be in the range of approximately 1.0 mm to 1.5 mm. For intermediate arteries, the height of the projections will be in the range of approximately 0.75 mm to 1.0 mm, and for small arteries, the height of the projections will be in the range of approximately 0.5 mm to 1.0 mm.

As should be appreciated by those skilled in the art the number of projections used in any device will also be a considerable factor in the amount of securement against migration provided thereby. Thus, as a general proposition, the more projections utilized the less "penetration" or "burrowing" will necessary for good securement against migration.

Figure 7:
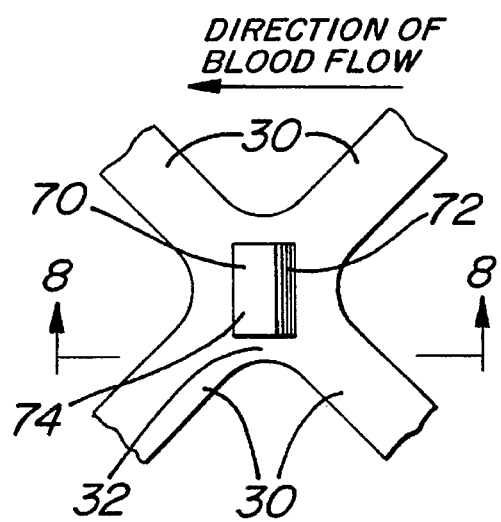
FIG. 7 is a plan view of a portion of yet another alternative embodiment of a graft constructed in accordance with this invention.
Figure 8:
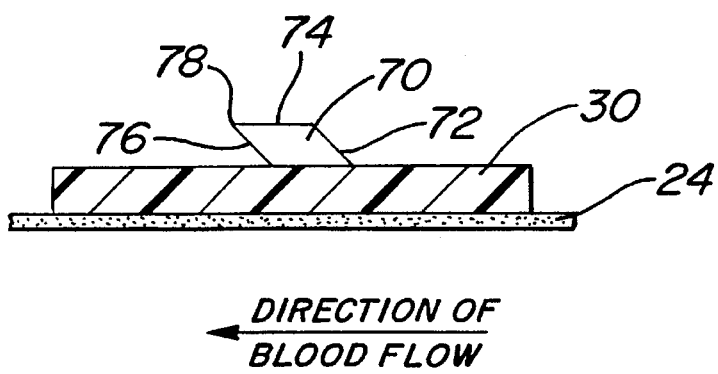
FIG. 8 is an enlarged sectional view taken along line 8—8 of FIG. 7.

In FIGS. 7 and 8, there is shown an alternative construction of locking projections constructed in accordance with the teaching of this invention. Those projections are of a general "wedge" shape and designated by the reference number 70. As should be appreciated by those skilled in the art the wedge shaped projections somewhat simpler construction to the "arrow-head" shaped projections 40, and hence will likely be easier to manufacture.

As can be seen in FIG. 8, each of the wedge shaped projections 70 includes a leading surface 72 defining the "front face" of the "wedge." The leading surface 72 extends upward at an acute angle to the exterior surface of the stent and terminates at the top surface 74 of the projection 70. The top surface 74 is generally planar and is either parallel to the plane of the stent portion from which it projects (as shown) or inclines upward in the direction of blood flow. Each projection also includes a trailing surface 76 which inclines upward in the direction of the blood flow to terminate at the top surface 74 in a penetration edge 78. Thus, as can be appreciated, each of the projections 70 also includes portions which are preferentially oriented at an acute angle to the direction of blood flow.

It should be pointed out that anchoring projections constructed in accordance with this invention can take numerous other shapes and sizes than those shown herein. In this regard, the projections need not include sharp edges and/or planar surfaces or points, and can be rounded, domed, or any other suitable shape, so long as they are preferentially oriented to project or extend at some acute a angle to the direction of fluid flow, whereupon the force applied to them by the fluid flowing through the vessel, duct, or lumen, in which the device to be secured by them flows produces on each of them a force component extending in the direction of the fluid flow and a force component extending perpendicularly to that direction. As discussed above this action causes the projections to tightly engage (and not necessarily penetrate) the interior of the wall of the vessel, duct, or lumen to fixedly secure the device in place against migration.

Without further elaboration the foregoing will so fully illustrate my invention that others may, by applying current or future knowledge, adopt the same for use under various conditions of service.

I claim:

1. An intraluminal medical device for securement within a vessel, duct, or lumen of a living being, the vessel, duct, or lumen having an interior surface, said device comprising a tubular member and anchoring means, said tubular member having a passageway extending therethrough and an outer periphery, said tubular member being arranged to have a body fluid flow through said passageway in a first direction when said device is located within the vessel, duct, or lumen, whereupon a force is applied to said tubular-member, said anchoring means being located adjacent said outer periphery of said tubular member and comprising plural projections arranged for engagement with the interior surface of the vessel, duct, or lumen, each of said projections having a leading portion located in the upstream direction of the fluid flow and a trailing portion located in the downstream direction thereof, said trailing portion including at least one surface preferentially oriented to extend at an acute angle to the first direction, whereupon the force applied to said tubular member by the fluid flowing through said passageway produces on each of said projections a force component to cause said at least one surface to tightly engage the interior surface of the vessel, duct, or lumen to fixedly secure said device in place.

2. The device of claim 1 wherein said at least one surface is inclined upward in the first direction.

3. The device of claim 2 wherein each of said projections includes a leading surface, a top surface, and a trailing surface, and wherein said at least one surface is said top surface.

4. The device of claim 2 wherein each of said projections includes a leading surface, a top surface, and a trailing surface, and wherein said at least one surface is said trailing surface.

5. The device of claim 2 wherein each of said projections includes a leading surface, a top surface, and a trailing surface, and wherein said at least one surface is said top surface and said trailing surface.

6. The device of claim 1 wherein each of said projections includes a leading surface, a top surface, and a trailing surface, said trailing surface meeting said top surface to form at least one penetrating edge.

7. The device of claim 6 wherein said penetrating edge forms a portion of a point.

8. The device of claim 7 wherein each of said projections include plural points.

9. The device of claim 1 wherein said tubular member is a stent.

10. The device of claim 9 wherein said stent is expandable from a contracted state to an expanded state, said anchoring means engaging the interior surface of the vessel, duct, or lumen when said stent is in said expanded state to secure said device in place.

11. The device of claim 10 wherein said stent comprises a plurality of interconnected movable links.

12. The device of claim 11 wherein said links are arranged in either diamond-like shaped configurations or in zig-zig shaped configurations.

13. The device of claim 10 wherein said device is an endovascular graft, said endovascular graft additionally comprising a graft sleeve, said sleeve being coupled to said stent and having an outer surface and inner passageway through which the body fluid flows in the first direction to apply the force to said projections.

14. The device of claim 13 wherein said stent is located on said outer surface of said sleeve.

15. The endovascular graft of claim 13, wherein said graft sleeve comprises a plurality of longitudinally extending pleats.

\* \* \* \* \*